United States Patent
Jochinsen (10) Patent No.: US 10,895,699 B2
(45) Date of Patent: Jan. 19, 2021

(54) METAL WIRE FOR OPTICAL FIBER CABLE AND STRAIN RELIEF

(71) Applicant: NOVARTIS AG, Basel (CH)

(72) Inventor: Mauricio Jochinsen, Fountain Valley, CA (US)

(73) Assignee: Alcon Inc., Fribourg (CH)

( * ) Notice: Subject to any disclaimer, the term of this patent is extended or adjusted under 35 U.S.C. 154(b) by 23 days.

(21) Appl. No.: 16/012,169

(22) Filed: Jun. 19, 2018

(65) Prior Publication Data

US 2019/0011646 A1    Jan. 10, 2019

Related U.S. Application Data

(60) Provisional application No. 62/529,316, filed on Jul. 6, 2017.

(51) Int. Cl.
| | | |
|---|---|---|
| *G02B 6/38* | (2006.01) | |
| *G02B 6/44* | (2006.01) | |
| *A61B 3/00* | (2006.01) | |
| *A61B 90/30* | (2016.01) | |
| *A61F 9/007* | (2006.01) | |

(52) U.S. Cl.
CPC .......... *G02B 6/3887* (2013.01); *A61B 3/0008* (2013.01); *A61B 90/30* (2016.02); *G02B 6/4429* (2013.01); *G02B 6/4478* (2013.01); *A61B 2090/306* (2016.02); *A61F 9/007* (2013.01); *G02B 6/4402* (2013.01); *G02B 6/4413* (2013.01); *G02B 6/4416* (2013.01); *G02B 6/4434* (2013.01)

(58) Field of Classification Search
CPC .. G02B 6/3887; G02B 6/4429; G02B 6/4478; G02B 6/4402; G02B 6/4413; G02B 6/4416; G02B 6/4434; A61B 3/008; A61B 2090/306; A61B 90/30; A61F 9/007

See application file for complete search history.

(56) References Cited

U.S. PATENT DOCUMENTS

| | | | |
|---|---|---|---|
| 4,557,558 A | 12/1985 | Bresser | |
| 5,195,158 A | 3/1993 | Bottoms, Jr. et al. | |
| 9,056,201 B1* | 6/2015 | Hamilton | A61N 5/1017 |
| 9,610,411 B2* | 4/2017 | Clancy | A61B 10/0233 |
| 9,795,505 B2 | 10/2017 | Yu | |
| 10,085,883 B2 | 10/2018 | Auld | |
| 2003/0006333 A1* | 1/2003 | Cooper | B65H 75/18 |
| | | | 242/400.1 |

(Continued)

FOREIGN PATENT DOCUMENTS

| | | |
|---|---|---|
| DE | 19624967 A1 | 1/1998 |
| EP | 0908749 A1 | 4/1999 |

OTHER PUBLICATIONS

Massa. "Fiber Optic Telecommunication." in: Fundamentals of Photonics [online]. SPIE, 2000 [retrieved Sep. 16, 2016 pp. 293-347. Retrieved from the Internet <URL:https://www.spie.org/Documents/Publications/00%20STEP%20Module%2008.pdf>.

(Continued)

*Primary Examiner* — Peter Radkowski (57) ABSTRACT

Various optical fiber cables and systems and methods associated therewith are disclosed herein. An optical fiber cable may include a jacket, an optical fiber and a metal wire disposed within a passage defined by the jacket. The metal wire may be coupled to the optical fiber.

10 Claims, 5 Drawing Sheets

(56) References Cited

U.S. PATENT DOCUMENTS

| | | | |
|---|---|---|---|
| 2006/0149194 A1* | 7/2006 | Conston | A61B 17/32002 604/294 |
| 2007/0100235 A1* | 5/2007 | Kennedy | A61B 6/504 600/434 |
| 2007/0255264 A1 | 11/2007 | Hickingbotham | |
| 2008/0091146 A1* | 4/2008 | Solovay | A61F 5/003 604/174 |
| 2010/0173866 A1* | 7/2010 | Hee | A61F 9/0017 514/54 |
| 2012/0191064 A1* | 7/2012 | Conston | A61F 9/00727 604/506 |
| 2015/0099995 A1* | 4/2015 | Clancy | A61B 10/0233 600/567 |
| 2015/0223976 A1* | 8/2015 | Bouch | A61F 9/008 606/4 |
| 2016/0143776 A1* | 5/2016 | Rotenstreich | A61F 9/0008 604/21 |
| 2018/0132963 A1 | 5/2018 | Diao | |

OTHER PUBLICATIONS

Specialty Fiber Optic Cable. Catalog. AFL, 2015.
Broadband Applications & Construction Manual. Products manual. COMMSCOPE, 2014.
Fiber Optic Cables in AV Systems. White paper [online]. EXTRON, Jun. 2012 [retrieved on Sep. 16, 2016]. Retrieved from the Internet <URL:https://www.extron.com/technology/library.aspx?tabid=0>.
Fiber Optic Cables, Assemblies, Connectors and Accessories. Catalog. LEONI, Sep. 2007.
Steenbergen. Everything You Always Wanted to Know About Optical Networking—But Were Afraid to Ask. Slide presentation. NANOG 57, Feb. 2013, Orlando, Florida.
Botha et al. OSP Fiber Optics Civil Works Guide. The Fiber Optic Association, Inc., 2015.
Fiber Types in Gigabit Optical Communications. White paper [online]. CISCO, 2008 [retrieved on Sep. 16, 2016]. Retrieved from the Internet <URL:https://www.cisco.com/c/en/us/products/collateral/interfaces-modules/transceiver-modules/white_paper_c11-463661.pdf>.

* cited by examiner

METAL WIRE FOR OPTICAL FIBER CABLE AND STRAIN RELIEF

CROSS-REFERENCE TO RELATED APPLICATIONS

This application claims the benefit of U.S. Provisional Application No. 62/529,316, filed Jul. 6, 2017, the entire contents of which are incorporated herein by reference.

BACKGROUND

Optical fiber cables are cables that are used in a variety of different applications to transmit light. Optical fiber cables may also be referred to as "optical cables" or "fiber optic cables." While optical fiber cables may have a number of different configurations, optical fiber cables typically include an optical fiber with one or more additional layers of strengthening and supporting material. Optical fiber cables used in many commercial applications may include two to five layers, including the optical fiber and additional layers. The optical fiber includes a core for light transmission and an outer cladding that surrounds the core.

Handling of optical fiber cables may be challenging due to the intrinsic fragility of the core of the optical fiber. In applications such as telecommunications, military, material processing, and automotive, and others, the optical fiber cables, once connected, remain stationary most of the time. Therefore, generally, optical fiber cables may be designed for minimum handling during installation.

SUMMARY

In an exemplary aspect, the present disclosure is directed to an optical fiber cable. The optical fiber cable may include a jacket, an optical fiber disposed in the jacket, and a metal wire disposed in the jacket and coupled to the optical fiber.

Another aspect is directed to a system for providing light to a surgical site. The system may include a light source, a medical instrument, and an optical fiber cable. The optical fiber cable may include a proximal end coupled to the light source, a distal end coupled to the medical instrument, a jacket, an optical fiber disposed within a passage defined by the jacket, and a metal wire disposed within the passage and coupled to the optical fiber. The optical fiber cable may optically couple the light source to the medical instrument.

A further aspect is directed to a method for illuminating an eye of a patient. The method may include disposing a distal end of a medical instrument in the eye and carrying light from a light source through an optical fiber cable to the medical instrument such that the light emanates from the medical instrument in the eye of the patient. The optical fiber cable may include a jacket defining a passage, an optical fiber disposed in the passage, and a metal wire disposed in the passage and coupled to the optical fiber.

The different aspects may include one or more of the following features. The optical fiber may include a core surrounded by an outer cladding that has a refractive index that is lower than a refractive index of the core. An adhesive may couple the optical fiber to the metal wire. The optical fiber may be wound around the metal wire. The optical fiber may be wound around the metal wire at a frequency of about 0.5 turn per meter of the metal wire to about 5 turns per meter of the metal wire. The optical fiber cable may further include a polymer tubing disposed in the jacket, wherein the optical fiber and the metal wire are disposed within a passaged defined by the polymer tubing. The optical fiber cable may further include a strengthening member disposed between the polymer tubing and the jacket. A supply conduit may be disposed in passage defined by the jacket. The supply conduit may form a hollow tube configured to supply a fluid to the medical instrument. Electrical wiring may be disposed in of the passage defined by the jacket. The electrical wiring may be configured to conduct electricity to the medical instrument. An end connector may couple the proximal end of the optical fiber cable to the light source. The end connector may include a first end, a second end, and an opening formed in the first end and extending to the second end. The optical fiber may extend through the opening in the first end to the second end. The optical fiber may include a glass core surround by an outer cladding that has a refractive index that is lower than a refractive index of the glass core. The metal wire may include at least one metal selected from the group consisting of stainless steel, spring steel, and shape memory steel. The optical fiber may be wound around the metal wire, and an adhesive may adhere the optical fiber to the metal wire. The medical instrument may include an optical element disposed at a distal end of the medical instrument and configured to receive light from the light source. The medical instrument may include a light cannula.

The different aspects may include one or more of the following features. Electricity may be conducted to the medical instrument through electrical wiring disposed within the passage defined by the jacket; fluid may be supplied to the medical instrument through a supply conduit disposed within of the passage defined by the jacket; or both. At least a portion of the optical fiber cable may be manipulated into a shape that follows a contour of the patient. The optical fiber cable may hold the shape that follows the contour of the patient. At least a portion of the optical fiber cable may be disposed on the patient and have a pre-defined shape that follows a contour of the patient. The metal wire may include a shape memory metal. An adhesive may couple the optical fiber to the metal wire.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate implementations disclosed herein and together with the description, serve to explain the principles of the present disclosure.

DETAILED DESCRIPTION

For the purposes of promoting an understanding of the principles disclosed herein, reference will now be made to the implementations illustrated in the drawings and specific language will be used to describe the example implementations. It will nevertheless be understood that no limitation of the scope of the disclosure is intended. Any alterations and further modifications to the described devices, medical instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations described herein. For simplicity, in some instances the same reference numbers are used throughout the drawings to refer to the same or like parts.

The present disclosure generally relates to optical fiber cables and, more particularly, in some embodiments, to optical fiber cables for use in medical applications. In accordance with example embodiments disclosed herein, optical fibers cables are provided that include a metal wire to reduce strain on the optical fiber. By way example, the metal wire may be coupled to the optical fiber, such that the tensile strength may be increased, thus reducing damage to the optical fiber when the optical fiber cable may be manipulated, such as during surgery and/or manufacturing. In addition, by attachment of the optical fiber to the metal wire, insertion of the optical fiber into a jacket of the optical fiber cable may be easier, as the metal wire provides support to the optical fiber. The metal wire may also provide an electrical connection that can be used, for example, for grounding of the medical instrument to which the optical fiber is connected or for a continuity check. Further, the metal wire may include a shape memory alloy so that contours of the optical fiber cable may be pre-defined during manufacturing. In addition, certain materials such stainless steel may hold their shape so the contour of the optical fiber cable may be defined as desired, for example, during surgery preparation.

Figure 1:
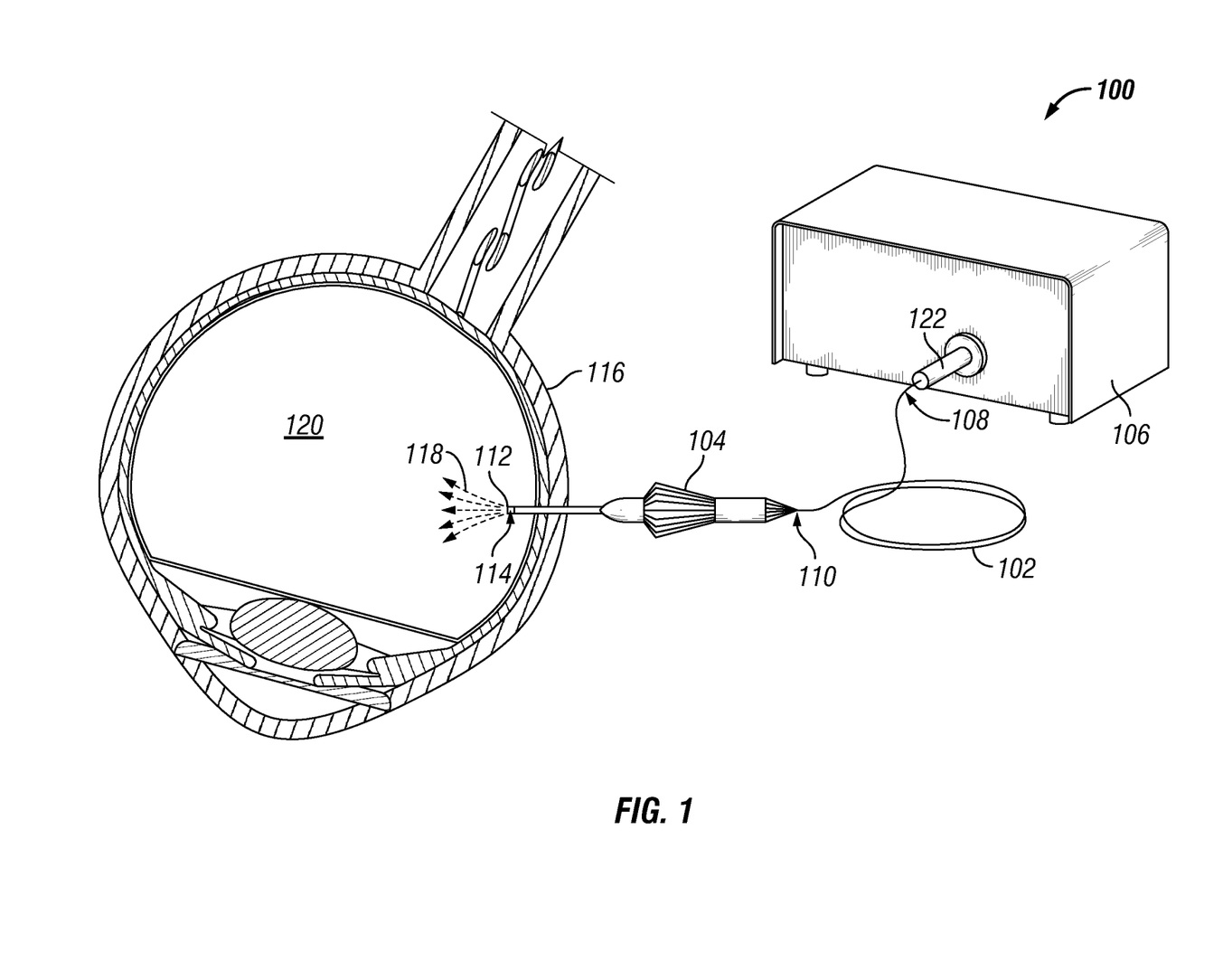
FIG. 1 is a schematic illustration of an example of a system that includes an optical fiber cable.

FIG. 1 is a schematic illustration of an example system 100 that includes an optical fiber cable 102. As illustrated, the system 100 further includes a medical instrument 104 coupled to the optical fiber cable 102. The optical fiber cable 102 may be coupled to a light source 106 at a proximal end 108 and to the medical instrument 104 at a distal end 110. The optical fiber cable 102 may be configured to releasably connect to the medical instrument 104 and/or to the light source 106. The optical fiber cable 102 may optically couple the light source 106 to the medical instrument 104. Light from the light source 106 may travel through the optical fiber cable 102 to the medical instrument 104, finally emanating from an optical element 112 at distal end 114 of the medical instrument 104. As illustrated, the distal end 114 of the medical instrument 104 may be disposed in an eye 116 so that emanated light 118 may illuminate an interior portion 120 of the eye 116.

The medical instrument 104 may be any of a variety of medical instruments that may be used in medical applications, including, but not limited to, a vitrectomy instrument with an illumination fiber or fibers, an infusion cannula, a trocar cannula, a laser instrument, an illumination instrument (e.g., a chandelier lighting system, an endoilluminator, etc.). In the illustrated embodiment, the medical instrument 104 includes the optical element 112 integrated into the medical instrument 104 at the distal end 114 of the medical instrument 104. While the medical instrument 104 shown on FIG. 1 is a handheld medical instrument, example embodiments are intended to include medical instruments that are not handheld (e.g., a light cannula, such as a light cannula 800 as shown on FIG. 8). Light source 106 may include any suitable source for providing light for delivery through the optical fiber cable 102, including, but not limited to, an incandescent light source, a light-emitting diode (LED) light source, a phosphor light source, or a laser light source. Non-limiting examples of laser light sources may include, but are not limited to, monochromatic (e.g., infrared, visible) laser light sources, multi-spectral laser light sources, or supercontinuum white laser light sources. The optical fiber cable 102 carries light from the light source 106 to the medical instrument 104. An end connector 122 couples the optical fiber cable 102 to the light source 106.

Figure 2:
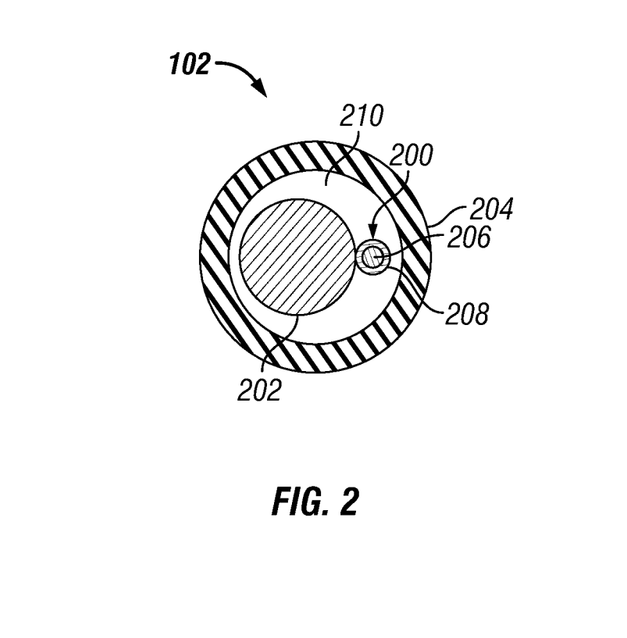
FIG. 2 is a cross-sectional view of an example optical fiber cable.

FIG. 2 shows a cross-sectional view of an example optical fiber cable 102 shown in FIG. 1. As illustrated, the optical fiber cable 102 includes an optical fiber 200 coupled to a metal wire 202. The optical fiber cable 102 further includes a jacket 204 surrounding the optical fiber 200 and the metal wire 202. The optical fiber 200 may have any of a variety of configurations. In the illustrated embodiment, the optical fiber 200 includes an optically transmissive core 206 surrounded by an outer cladding 208. In some instances, the outer cladding 208 may have a refraction index that is lower than the core 206 so that light travelling down the core 206 should typically be reflected off the outer cladding 208 and remain within the core 206. In some implementations, the core 206 may be made from various materials, including, but not limited to, glass, plastic, and combinations thereof. In some embodiments, the core 206 may be or include a glass core. In some instances, the core 206 may be formed from or include a polymer. The outer cladding 208 may be made from various materials, including, but not limited to, glass, plastic, and combinations thereof.

While some implementations of the optical fiber cable 102 include a single optical fiber 200, the scope of the disclosure is not so limited. Rather, in other implementations, the optical fiber cable 102 may include a bundle or plurality of optical fibers. The optical fibers of the plurality of optical fibers may be similar to the optical fibers 200 described herein. Further, one or more of the optical fibers of the plurality of optical fibers may be different from one or more other optical fibers of the plurality of optical fibers.

By coupling the optical fiber 200 to the metal wire 202, the optical fiber 200 may experience less strain, for example, during use and/or manufacturing, to protect the optical fiber 200 from mechanical stress. The metal wire 202 may be able to absorb energy and plastically deform without fracturing, thus protecting the optical fiber 200, due to a number of properties of the material forming the metal wire 202, including its tensile strength, elastic modulus, brittleness, and cross-section diameter. In addition, the metal wire 202 may be considered ductile while the optical fiber 200 may be considered brittle. Further, the metal wire 202 may be less susceptible to deformation from small radius bends as compared to polymeric tubes in which the optical fibers 200 are ordinarily disposed for protection. As a result, the metal wire 202 protects the optical fiber 200 and may prevent the optical fiber 200 from being damaged, thereby reducing risk in a surgical environment.

In some embodiments, the metal wire 202 may have a circular cross-section, as shown in FIG. 2. In such instances, the metal wire 202 may have a diameter that is from 10 to 1000 times greater than the diameter of the optical fiber 200. In some implementations, while the optical fiber 200 transmits light, the metal wire 202 may be utilized to provide an electrical connection, depending on the particular application. For example, the metal wire 202 may be connected to a medical instrument 104 (e.g., the medical instrument 104 shown on FIG. 1) to ground the medical instrument. By way of further example, the metal wire 202 may be connected to a medical instrument (e.g., the medical instrument 104 shown on FIG. 1) and be utilized to provide a continuity check.

Any suitable technique may be used for coupling the optical fiber 200 to the metal wire 202. Suitable techniques include, but are not limited to, the use of adhesives, mechanical fasteners, or combinations thereof, to join the metal wire 202 to the optical fiber 200. In some embodiments, adhesives that may be used to join the metal wire 202 to the optical fiber 200 include epoxy glues. Epoxy glues may be self-hardenable, ultraviolet curable, thermal activated, or use an external catalyst for curing, among other reaction mechanisms.

The metal wire 202 may be formed from a variety of metals, including, but not limited to, stainless steel, spring steel, or shape memory steel. Spring steel refers to a wide range of steels that are used in variety of application. Spring steels are capable of elastic deformation such that the steels return to an original shape, for example, after an applied bending or twisting force is removed, even despite significant bending or twisting. Spring steels are typically classified as a low alloy, medium carbon, or high carbon steel with a high yield strength. Examples of spring steels that may be used include, but are not limited to, steel classified as SAE 1074/1075, SAE 1080 (ASTM A228), SAE 1095 (ASTM A684), SAE 5160 (ASTM A680), 50CrV4, SAE 9255, or 301 stainless steel, among others. In some embodiments, a spring steel considered music wire, which may be classified as ASTM A228, may be used.

Shape memory steel refers to a variety of alloys having mechanical properties that permit the steel to "remember" an initial or original shape and return to the initial shape upon being heated above a transformation temperature after the steel has been deformed. Examples of alloys for shape memory steels that may be used include, but are not limited to, nickel-titanium alloys, copper-aluminum-nickel alloys, copper-zinc aluminum alloys, iron-manganese-silicon alloys, and combinations thereof.

With continued reference to FIG. 2, the optical fiber 200 and the metal wire 202 may be disposed within a passage 210 defined by the jacket 204. The jacket 204 functions as a protective sheathing to protect the optical fiber 200 disposed therein from the external environment. In some instances, the jacket 204 may be made from various materials, including, but not limited to, plastics, metals, braided fabric, and combinations thereof. Examples of plastics that may be used include, but are not limited to, polyethylene, polyvinyl chloride, polyurethane, or combinations thereof.

Figure 3:
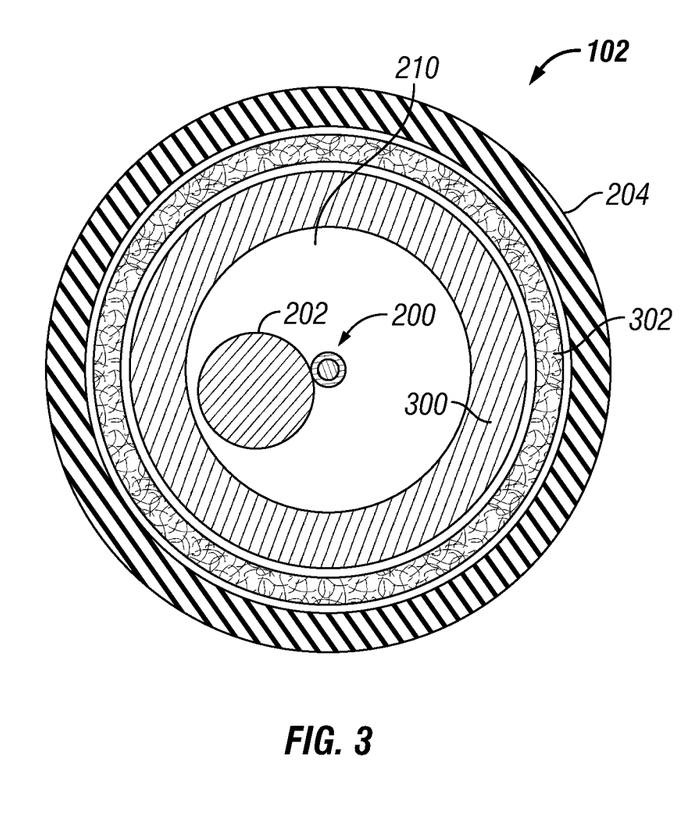
FIG. 3 is a cross-sectional view of another example optical fiber cable.

FIG. 3 shows a cross-sectional view of another example optical fiber cable 102. The example optical fiber cable 102 shown in FIG. 3 includes an optical fiber 200 coupled to a metal wire 202. The optical fiber 200 and the metal wire 202 are both disposed within a passage 210 defined by the jacket 204. However, the illustrated embodiment further includes additional layers between the jacket 204 and the optical fiber 200 and metal wire 202 disposed therein. Particularly, the example optical fiber cable 102 of FIG. 3 further includes a polymer tubing 300 and a strengthening member 302.

In some embodiments, the polymer tubing 300 may be disposed between the jacket 204 and the optical fiber 200, as shown in FIG. 3. More particularly, in some embodiments, the polymer tubing 300 may be disposed between the strengthening member 302 and the optical fiber 200, as also shown in FIG. 3. As illustrated, the optical fiber 200 and the metal wire 202 may be disposed within a portion of the passage 210 that is disposed within the polymer tubing 300. The polymer tubing 300 may be made from various materials, including, but not limited to, polypropylene, polyethylene, polyvinyl chloride, polyurethane, or combinations thereof.

In some embodiments, the strengthening member 302 may be disposed between the polymer tubing 300 and the jacket 204, as shown in FIG. 3. The strengthening member 302 may be included in the optical fiber cable 102, for example, to reduce stress on the optical fiber 200 in combination with the metal wire 202. For example, the strengthening member 302 may function to receive stress loads, thereby reducing possible fatigue on the optical fiber 200. The strengthening member 302 may be made from various materials, including, but not limited to, aramid fibers, steel wire, or fiberglass epoxy rods.

Figure 4:
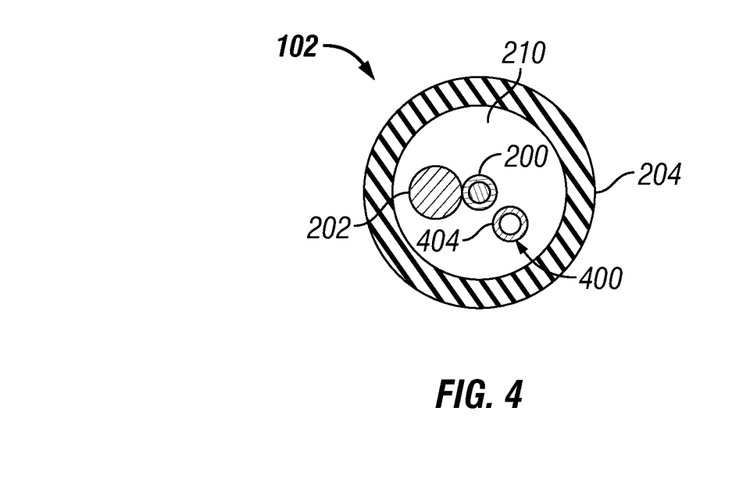
FIG. 4 is a cross-sectional view of another example optical fiber cable.

FIG. 4 shows a cross-sectional view of another example optical fiber cable 102. The example optical fiber cable 102 of FIG. 4 includes an optical fiber 200 coupled to a metal wire 202. The optical fiber 200 and the metal wire 202 are both disposed in a passage 210 defined by a jacket 204. However, the illustrated example further includes a supply conduit 400 disposed within the passage 210. The supply conduit 400 may be used to supply a fluid, such as air, carbon dioxide, oxygen, or any other fluid, to a medical instrument (e.g., such as medical instrument 104 shown in FIG. 1). In some embodiments, the supply conduit 400 may be in the form of a hollow tube 404, as shown on FIG. 4. The hollow tube 404 may be made from various materials, including, but not limited to, polypropylene, polyethylene, polyvinyl chloride, polyurethane, or combinations thereof. While the supply conduit 400 is shown disposed within the passage 210 of the optical cable 102 that lacks a polymer tubing (e.g., the polymer tubing 300 as shown in FIG. 3) or a strengthening member (e.g., the strengthening member 302 as shown in FIG. 3), it should be understood that the supply conduit 400 may be used in combination with other configurations of the optical fiber cable 102, such as the embodiment shown on FIG. 3. In such implementations, the supply conduit 400 may be dispose within the portion of the passage 210 disposed within the polymer tubing 300. Still further, a supply conduit, such as the supply conduit 400, may be incorporated into any of the other example optical fiber cables described herein, including that shown in FIG. 2 or 5.

Figure 5:
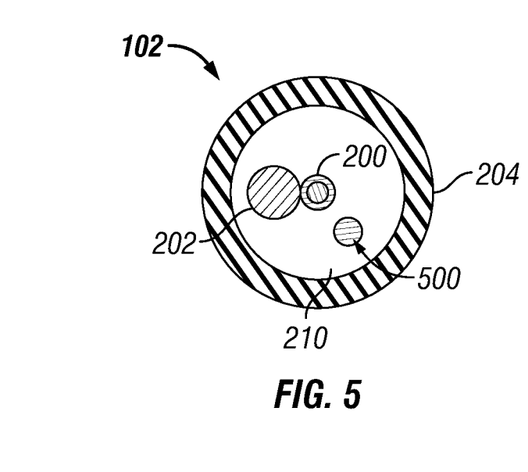
FIG. 5 is a cross-sectional view of another example optical fiber cable.

FIG. 5 shows a cross-sectional view of another example optical fiber cable 102. The optical fiber cable 102 illustrated on FIG. 5 includes the optical fiber 200 coupled to the metal wire 202. The optical fiber 200 and the metal wire 202 are disposed within a passage 210 defined by a jacket 204. However, the illustrated example further includes electrical wiring 500 disposed within the passage 210. The electrical wiring 500 be utilized to supply electricity to a medical instrument (e.g., the medical instrument 104 shown in FIG.

1). The electrical wiring 500 may be made from various materials for conducting electricity, including, but not limited to, copper or aluminum. While the example optical fiber cable 102 shown in FIG. 5 is not shown as including a polymer tubing (e.g., polymer tubing 300 as shown in FIG. 3) or a strengthening member (e.g., strengthening member 302 as shown in FIG. 3), it should be understood that the electrical wiring 500 may be used in combination with other configurations of the optical fiber cable 102, such as the embodiment shown on FIG. 3. Still further, electrical wiring, such as the electrical wiring 500, may be incorporated into any of the other example optical fiber cables described herein, including that shown in FIG. 2 or 4.

Figure 6:
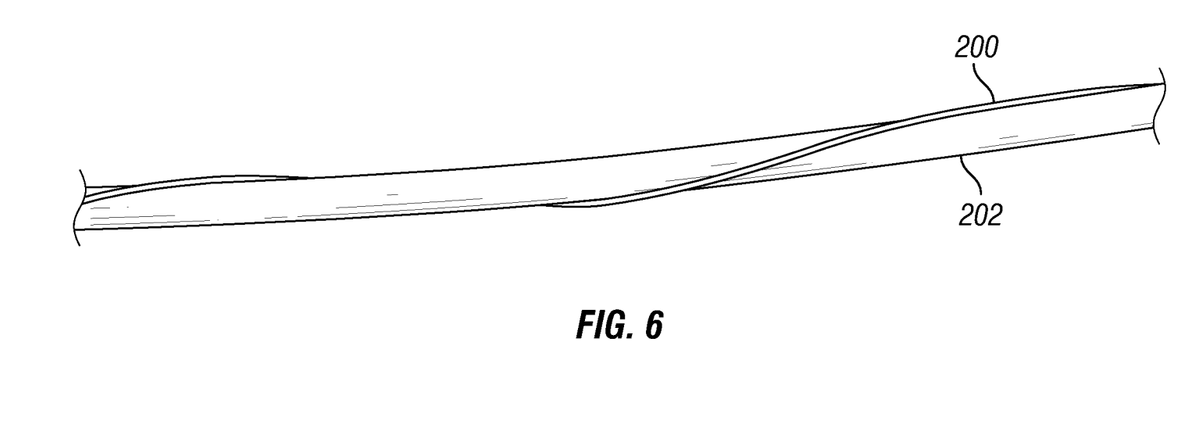
FIG. 6 is a perspective partial view showing an example optical fiber coupled to a metal wire.

FIG. 6 is a perspective view showing a portion of an embodiment of an optical fiber 200 coupled to a metal wire 202. The example of FIG. 6 may include a jacket, such as jacket 204 as shown on FIGS. 2-5. However, for clarity, a jacket (e.g.,) is not illustrated on FIG. 6 in order to illustrate the configuration of the optical fiber 200 and the metal wire 202. In the illustrated example, the optical fiber 200 is wound around the metal wire 202, such as in a helical manner. When wound around the metal wire 202, the optical fiber 200 has a length that is greater than the length of the metal fiber 2. Accordingly, when stretched during operation, the metal wire 202, due to its shorter length, experiences a tensile stress before the optical fiber 200 experiences a tensile stress. Further, winding the optical fiber 200 around the metal wire 202 can be viewed as produces slack in the optical fiber 200. When the metal wire 202 experiences a tensile force and, as a result, tensile elongation, the slack of the optical fiber 202 prevents the optical fiber 202 from experiencing the tensile stresses or elongation.

The optical fiber 200 may be wound around the metal wire 202 at any desired frequency. For example, the number of twists of the optical fiber 200 per length of the metal wire 200 may include, but is not limited to, about 0.5 turns of the optical fiber 200 per meter of metal wire 202, about 5 turns of the optical fiber 200 per meter of the metal wire, or any other desired number of twists of the optical fiber 200 per length of the metal wire 202. In some embodiments, the optical fiber 200 may be wound around the metal wire 202 at a frequency of about 1 turn of the optical fiber 200 per meter of metal wire 202 to about 2 turns of the optical fiber 200 per meter of the metal wire 202. In some embodiments, the optical fiber 200 may be wound around the metal wire 202 at a frequency of about 5 turns of the optical fiber 200 per 3 meters of metal wire 202. Winding of the optical fiber 200 around the metal wire 202 may include stretching the metal wire 202. For example, the metal wire 202 may be stretched between two points, such as with the use of one or more vises (not shown). The optical fiber 200 may then be wound around the stretched metal wire 202. An adhesive (not shown) may be applied over a portion or all of a of a length of the optical fiber 200, the metal wire 202, or both, for example, to bond the optical fiber 200 to the metal wire 202. Thereafter, the tension placed on the metal wire 202 may be removed. Once bonded, a jacket, such as the jacket 204 described above, may be installed over the combined optical fiber 200 and metal wire 202.

Figure 7A:
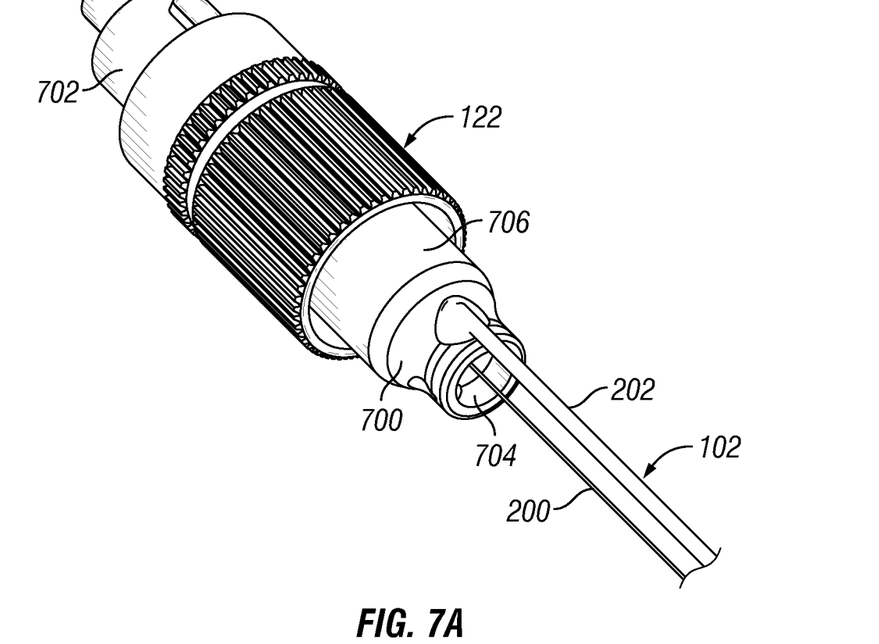
FIG. 7A is a perspective view showing an example optical fiber and metal wire coupled to an end connector.
Figure 7B:
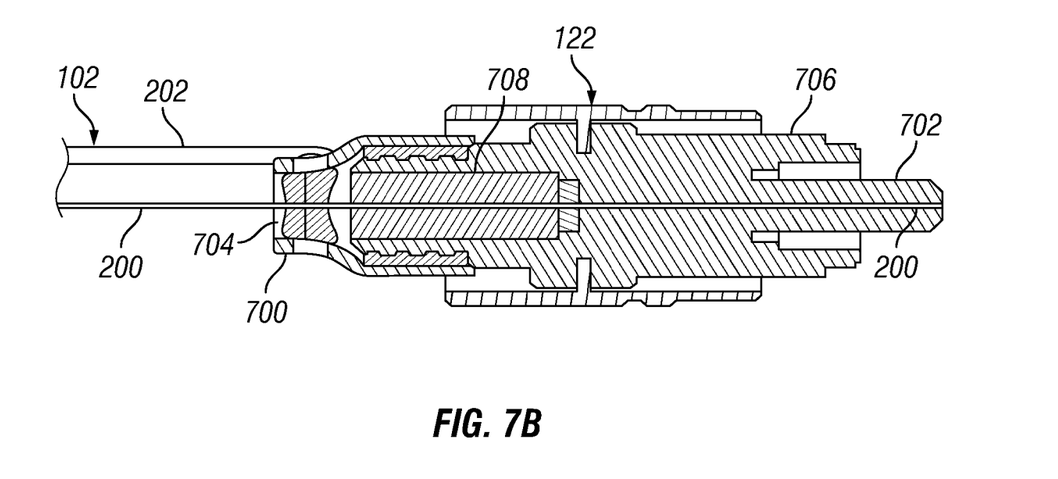
FIG. 7B is a cross-sectional view of the showing an example optical fiber and metal wire coupled to an end connector.

FIGS. 7A and 7B illustrate an example optical fiber cable 102 coupled to an end connector 122. The optical fiber cable 102 includes an optical fiber 200 and a metal wire 202. While, in some implementations, additional components, such as one or more of those illustrated in FIGS. 2-5 and described in the associated portions of the disclosure (e.g., a jacket, outer cladding, strengthening member, polymer tubing, supply conduit, or electrical wiring), may be included in the example shown in FIGS. 7A and 7B, such additional components are not shown in order to better illustrate the connection between the connector 122 and the metal wire 202 and optical fiber 200.

In the illustrated example, end connector 122 includes a first end 700 and a second end 702. The second end 702 of the end connector 122 is received into or coupled to a light source, such as the light source 106 shown in FIG. 1. The metal wire 202 may be coupled to the first end 700 of the end connector 122. Any suitable or applicable technique may be used to couple the metal wire 202 to the first end 700 of the end connector 122. Example coupling techniques include, but are not limited to, bonding, glue, or soldering. An opening 704 is formed in first end 700. The optical fiber 200 extends into a housing 706 of the end connector 122 through the opening 704. As illustrated in FIG. 7B, the optical fiber 200 extends through the housing 706 to the second end 702 of the end connector 122. In some instances, the optical fiber 200 may not extend to the second end 702 of the end connector 122. Rather, in some implementations, the optical fiber 200 may terminate at a location within the end connector 122 at a location other than the second end 702. The optical fiber 200 extends through a fiber holder 708 that is disposed in housing 706. Other implementations may exclude the fiber holder 708. In the illustrated example, the optical fiber 200 is coupled to the fiber holder 708. For example, the optical fiber 200 may be adhered, e.g., via glue, epoxy or other adhesive, or otherwise coupled to the fiber holder 708.

Figure 8:
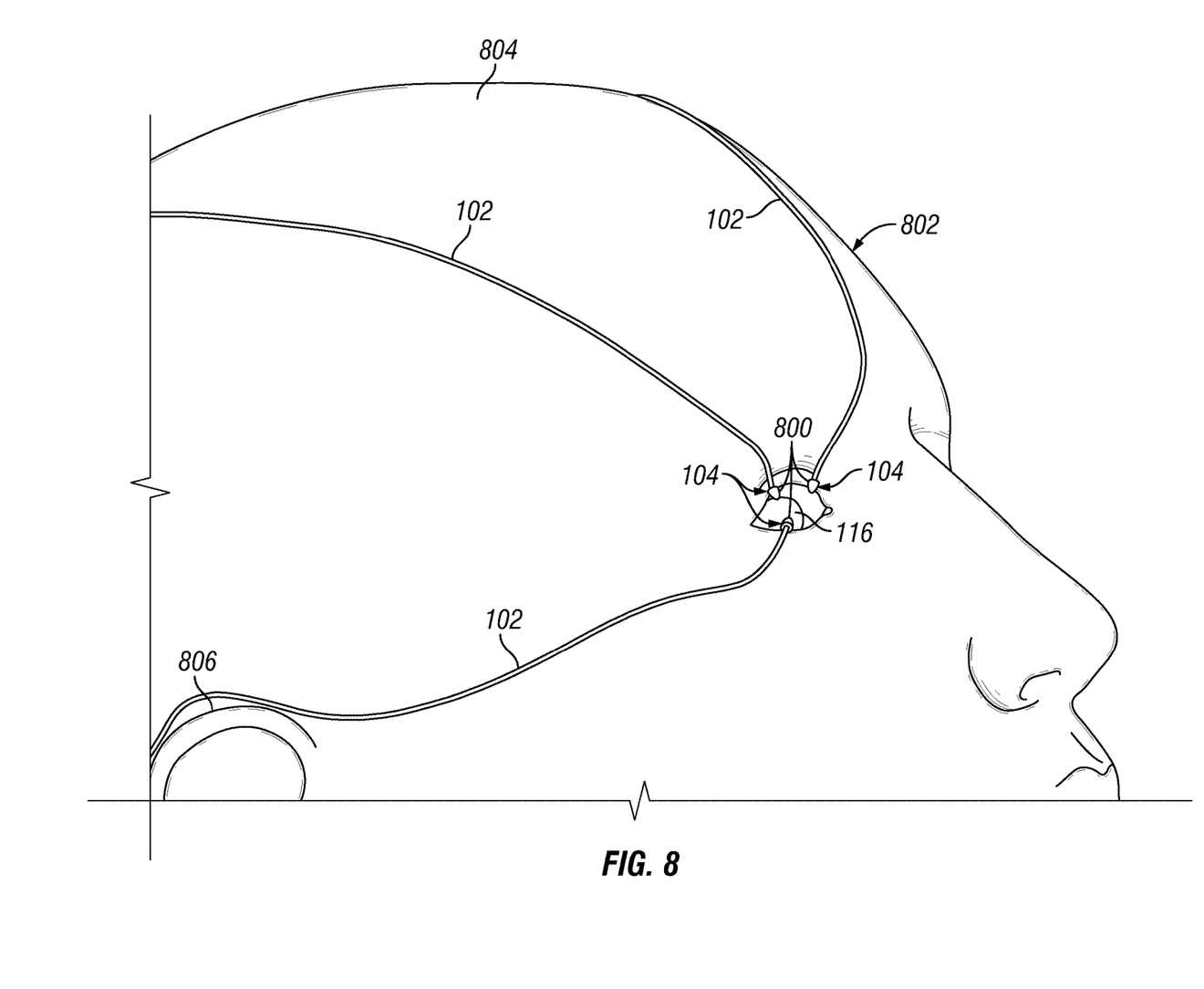
FIG. 8 is an illustration of the use of an example optical fiber cable.

FIG. 8 illustrates use of optical fiber cables 102. The optical fiber cables 102 may be any of the types falling within the scope described herein. Further, one or more of the optical fiber cables 102 may be different from one another. For example, one or more of the optical fibers may include additional or few components, such as such as one or more of those illustrated in FIGS. 2-5 and described in the associated portions of the disclosure (e.g., a jacket, outer cladding, strengthening member, polymer tubing, supply conduit, or electrical wiring), than another of the optical fiber cables 102.

In the illustrated embodiment of FIG. 8, the optical fiber cables 102 are coupled to medical instruments 104 in the form of light cannulas 800 that can emit light. However, in other implementations, the medical instruments 104 may be another type of medical instrument other than a light cannula. For example, one or more of the medical instruments 104 may be an infusion cannula, a trocar cannula, a laser instrument or another type of medical instrument that utilizes an optical fiber. The light cannulas 800 may be used for illumination in the eye 116 of a patient 802. As illustrated, the light cannulas 800 are disposed in the eye 116 of the patient 802. Light travels through the optical fiber cables 102 to the light cannulas 800 to provide illumination in the eye 116. While FIG. 8 illustrates the use of three of the optical fiber cables 102 and three of the light cannulas 800, additional or fewer optical fiber cables 102 or the light cannulas 800 may be used in other applications.

With continued reference to FIG. 8, in some embodiments, the optical fiber cables 102 may be manipulated to maintain a specific contour as desired in a specific application. In the illustrated embodiment, the optical fiber cable 102 has been manipulated to follow specific contours of the patient 802, such as head 804 or ear 806 of the patient 802. To maintain the specific contour, the optical fiber cables 102 includes a metal wire (e.g., such as the metal wire 202 shown in FIGS. 2-7B) made from a material as described herein. For example, the metal wire of one or more of the optical fiber cables 102 may be made of stainless steel (e.g., a stainless steel with a low elasticity) or a shape-memory alloy. As a result, the metal wire is capable of retaining a particular shape after bending. Advantageously, this would allow the optical fiber cables 102 to be manipulated into a desired shape, made to follow a desired contour, or manipulated into a desired location, for example, before, during, or after surgery. Alternatively, one or more of the optical fiber cables 102 may include a shape-memory allow so that one or more of the optical fibers cables 102 can be provided with a pre-defined shape that follows the contours of the patient 802.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A system for providing light to a surgical site, comprising:
    a light source;
    a medical instrument; and
    an optical fiber cable comprising:
        a proximal end coupled to the light source;
        a distal end coupled to the medical instrument;
        a jacket;
        an optical fiber disposed within a passage defined by the jacket; and
        a metal wire disposed within the passage and coupled to the optical fiber, the optical fiber cable optically coupling the light source to the medical instrument.

2. The system of claim 1, wherein the medical instrument comprises an optical element disposed at a distal end of the medical instrument and configured to receive light from the light source.

3. The system of claim 1, wherein the medical instrument comprises a light cannula.

4. The system of claim 1, wherein the optical fiber comprises a core surrounded by an outer cladding that has a refractive index that is lower than a refractive index of the core.

5. The system of claim 1, wherein an adhesive couples the optical fiber to the metal wire.

6. The system of claim 1, wherein the optical fiber is wound around the metal wire.

7. The system of claim 6, wherein the optical fiber is wound around the metal wire at a frequency of about 0.5 turn per meter of the metal wire to about 5 turns per meter of the metal wire.

8. The system of claim 1, further comprising a supply conduit disposed in the passage defined by the jacket, wherein the supply conduit is a hollow tube configured to supply a fluid to the medical instrument.

9. The system of claim 1, further comprising electrical wiring disposed in the passage defined by the jacket, wherein the electrical wiring is configured to conduct electricity to the medical instrument.

10. The system of claim 1, further comprising an end connector coupling the proximal end of the optical fiber cable to the light source, wherein the end connector comprises:
    a first end;
    a second end; and
    an opening formed in the first end and extending to the second end, wherein the optical fiber extends through the opening in the first end to the second end.

\* \* \* \* \*